(12) United States Patent
Thomas et al.

(10) Patent No.: US 9,283,032 B2
(45) Date of Patent: Mar. 15, 2016

(54) ELECTROSURGICAL INSTRUMENT

(75) Inventors: Rolf L. Thomas, West Sussex (GB); Martin P. H. Hoole, Wales (GB); Mark Bowles, Wales (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 1260 days.

(21) Appl. No.: 12/222,184

(22) Filed: Aug. 4, 2008

(65) Prior Publication Data
US 2009/0048592 A1 Feb. 19, 2009

Related U.S. Application Data

(60) Provisional application No. 61/006,768, filed on Jan. 30, 2008.

(30) Foreign Application Priority Data

Aug. 3, 2007 (GB) .................................. 0715152.5

(51) Int. Cl.
A61B 18/18 (2006.01)
A61B 18/14 (2006.01)

(52) U.S. Cl.
CPC .................................. *A61B 18/148* (2013.01)

(58) Field of Classification Search
CPC ................. A61B 18/148; A61B 18/14; A61B 2018/046; A61B 2018/1405; A61B 2018/00083; A61B 2018/1497; A61B 2218/001
USPC ........ 606/41, 48–50; 607/101, 102, 104, 105; 604/35, 114
See application file for complete search history.

(56) References Cited

U.S. PATENT DOCUMENTS 6,210,405 B1 * 4/2001 Goble et al. .................... 606/41
6,363,937 B1 4/2002 Hovda et al.

(Continued)

FOREIGN PATENT DOCUMENTS

JP 10-503941 4/1998
JP 2000-512526 9/2000

(Continued)

OTHER PUBLICATIONS

Search Report for corresponding UK Application No. GB0715152.5, date of search Nov. 28, 2007.
International Search Report and Written Opinion of the International Searching Authority issued in corresponding International Application No. PCT/GB2008/002480, mailed Oct. 27, 2008.
English Translation of Japanese Office Action for corresponding Japanese Application No. 2010-518728, date of issue Jan. 29, 2013.

(Continued)

Primary Examiner — Bhisma Mehta
Assistant Examiner — Bradley G Thomas, Jr.
(74) Attorney, Agent, or Firm — Nixon & Vanderhye, PC

(57) ABSTRACT

An electrosurgical instrument for the treatment of tissue in the presence of an electrically-conductive fluid medium comprises an instrument shaft (10), and an electrode assembly (12) at one end of the shaft. The electrode assembly (12) comprises a tissue treatment electrode (14) and a return electrode (18) which is electrically insulated from the tissue treatment electrode by means of an insulation member (16). The tissue treatment electrode (14) has an exposed surface for treating tissue, and the return electrode (18) has a fluid contact surface so as to define, in use, a conductive fluid path that completes an electrical circuit between the tissue treatment electrode and the return electrode. The tissue treatment electrode (14) is provided with at least one aperture (14a) through which vapor bubbles and/or particulate material can be aspirated from the region surrounding the tissue treatment electrode, and the tissue treatment electrode and the insulation member are disposed such that there is a gap therebetween forming an additional suction channel (25).

24 Claims, 10 Drawing Sheets

(56) References Cited

U.S. PATENT DOCUMENTS

| | | | |
|---|---|---|---|
| 6,482,202 B1 * | 11/2002 | Goble et al. | 606/41 |
| 6,565,561 B1 | 5/2003 | Goble et al. | |
| 6,780,180 B1 | 8/2004 | Goble et al. | |
| 7,150,746 B2 * | 12/2006 | DeCesare et al. | 606/41 |
| 2002/0068930 A1 | 6/2002 | Tasto et al. | |
| 2002/0107516 A1 * | 8/2002 | Sharkey et al. | 606/49 |
| 2005/0027235 A1 * | 2/2005 | Knudsen et al. | 604/20 |
| 2005/0277915 A1 | 12/2005 | DeCesare et al. | |

FOREIGN PATENT DOCUMENTS

| | | | |
|---|---|---|---|
| WO | 95-31144 | | 11/1995 |
| WO | 97-48346 | | 12/1997 |
| WO | WO 97/48346 | * | 12/1997 |
| WO | WO 97/78346 | | 12/1997 |
| WO | WO 99/03409 | | 1/1999 |

OTHER PUBLICATIONS

Patent Examination Report No. 1 for corresponding Australian Application No. 2008285528, date of issue Jan. 24, 2013.

Japanese Office Action/Reasons for Rejection for corresponding Japanese Application No. 2014-080893, mailing date Jan. 6, 2015.

English Translation of Japanese Office Action/Reasons for Rejection for corresponding Japanese Application No. 2014-080893, mailing date Jan. 6, 2015.

Search Report issued in corresponding Canadian Application No. 2,694,795, dated Nov. 21, 2014.

Office Action issued in corresponding Canadian Application No. 2,694,795, dated Dec. 2, 2014.

Examination Search Report in Canadian Application No. 2,694,795, dated Sep. 16, 2015.

Requisition (Office Action) issued in corresponding U.S. Appl. No. 2,694,795, dated Sep. 21, 2015.

* cited by examiner

ELECTROSURGICAL INSTRUMENT

RELATED APPLICATIONS

This application claims priority to United Kingdom Application No. 0715152.5, filed 3 Aug. 2007, and claims the benefit of U.S. Provisional Application No. 61/006,768, filed 30 Jan. 2008, the entire contents of each of which are hereby incorporated by reference.

BACKGROUND OF THE INVENTION

This invention relates to an electrosurgical instrument for the treatment of tissue in the presence of an electrically-conductive fluid medium, to electrosurgical apparatus including such an instrument, and to an electrode unit for use in such an instrument.

Endoscopic electrosurgery is useful for treating tissue in cavities of the body, and is normally performed in the presence of a distension medium. When the distension medium is a liquid, this is commonly referred to as underwater electrosurgery, this term denoting electrosurgery in which living tissue is treated using an electrosurgical instrument with a treatment electrode or electrodes immersed in liquid at the operation site. A gaseous medium is commonly employed when endoscopic surgery is performed in a distensible body cavity of larger potential volume in which a liquid medium would be unsuitable, as is often the case in laparoscopic or gastroenterological surgery.

Underwater surgery is commonly performed using endoscopic techniques, in which the endoscope itself may provide a conduit (commonly referred to as a working channel) for the passage of an electrode. Alternatively, the endoscope may be specifically adapted (as in a resectoscope) to include means for mounting an electrode, or the electrode may be introduced into a body cavity via a separate access means at an angle with respect to the endoscope—a technique commonly referred to as triangulation. These variations in technique can be subdivided by surgical speciality, where one or other of the techniques has particular advantages given the access route to the specific body cavity. Endoscopes with integral working channels, or those characteristics as resectoscopes, are generally employed when the body cavity may be accessed through a natural body opening—such as the cervical canal to access the endometrial cavity of the uterus, or the uretha to access the prostate gland and bladder. Endoscopes specifically designed for use in the endometrial cavity are referred to as hysteroscopes, and those designed for use in the urinary tract include cystoscopes, urethroscopes and resectoscopes. The procedures of transurethal resection or vaporisation of the prostate gland are known as TURP and EVAP respectively. When there is no natural body opening through which an endoscope may be passed, the technique of triangulation is commonly employed. Triangulation is commonly used during underwater endoscopic surgery on joint cavities such as the knee and the shoulder. The endoscope used in these procedures is commonly referred to as an arthroscope.

Electrosurgery is usually carried out using either a monopolar instrument or a bipolar instrument. With monopolar electrosurgery, an active electrode is used in the operating region, and a conductive return plate is secured to the patient's skin. With this arrangement, current passes from the active electrode through the patient's tissues to the external return plate. Since the patient represents a significant portion of the circuit, input power levels have to be high (typically 150 to 250 watts), to compensate for the resistive current limiting of the patient's tissues and, in the case of underwater electrosurgery, power losses due to the fluid medium which is rendered partially conductive by the presence of blood or other body fluids. Using high power with a monopolar arrangement is also hazardous, due to the tissue heating that occurs at the return plate, which can cause severe skin burns. There is also the risk of capacitive coupling between the instrument and patient tissues at the entry point into the body cavity.

With bipolar electrosurgery, a pair of electrodes (a tissue treatment electrode and a return electrode) are used together at the tissue application site. This arrangement has advantages from the safety standpoint, due to the relative proximity of the two electrodes so that radio frequency currents are limited to the region between the electrodes. However, the depth of effect is directly related to the distance between the two electrodes; and, in applications requiring very small electrodes, the inter-electrode spacing becomes very small, thereby limiting tissue effect and the output power. Spacing the electrodes further apart would often obscure vision of the application site, and would require a modification in surgical technique to ensure direct contact of both electrodes with the tissue.

The electrical junction between the return electrode and tissue can be supported by wetting of the tissue by a conductive solution such as normal saline. This ensures that the surgical effect is limited to the tissue treatment electrode, with the electric circuit between the two electrodes being completed by the tissue. One of the obvious limitations with the design is that the tissue treatment electrode must be completely buried in the tissue to enable the return electrode to complete the circuit. Another problem is one of the orientation even a relatively small change in application angle from the ideal perpendicular contact with respect to the tissue surface, will change the contact area ratio, so that a surgical effect can occur in the tissue in contact with the return electrode.

Cavity distension provides space for gaining access to the operation site, to improve visualisation, and to allow for manipulation of instruments. In low volume body cavities, particularly where it is desirable to distend the cavity under higher pressure, liquid rather than gas is more commonly used due to better optical characteristics, and because it washes blood away from the operative site.

Conventional underwater electrosurgery has been performed using a non-conductive liquid (such as 1.5% glycine) as an irrigant, or as a distension medium to eliminate electrical conduction losses. Glycine is used in isotonic concentrations to prevent osmotic changes in the blood when intravascular absorption occurs. In the course of an operation, veins may be severed, with resultant infusion of the liquid into the circulation, which could cause, among other things, a dilution of serum sodium which can lead to a condition known as water intoxication.

The applicants have found that it is possible to use a conductive liquid medium, such as normal saline, in underwater endoscopic electrosurgery in place of non-conductive, electrolyte-free solutions. Normal saline is the preferred distension medium in underwater endoscopic surgery when electrosurgery is not contemplated, or a non-electrical tissue effect such as laser treatment is being used. Although normal saline (0.9% w/v: 150 mmol/l) has an electrical conductivity somewhat greater than that of most body tissue, it has the advantage that displacement by absorption or extravasation from the operative site produces little physiological effect, and the so-called water intoxication effects of non-conductive, electrolyte-free solutions are avoided. The applicants have developed a bipolar instrument suitable for underwater electrosurgery using a conductive liquid. This electrosurgical instrument comprises an instrument body having a handpiece and an instrument shaft and an electrode assembly, at one end of the shaft. The electrode assembly comprises a tissue treatment (active) electrode which is exposed at the extreme distal end of the instrument, and a return electrode which is electrically insulated from the tissue treatment electrode and has a fluid contact surface spaced proximally from the exposed part of the tissue treatment electrode. In use of the instrument, the tissue treatment electrode is applied to the tissue to be treated whilst the return electrode, being spaced proximally from the exposed part of the tissue treatment electrode, is normally spaced from the tissue and serves to complete an electrosurgical current loop from the tissue treatment electrode through the tissue and the fluid medium. This electrosurgical instrument is described in the specification of our European Patent No. 771176.

The electrode structure of this instrument, in combination with an electrically-conductive fluid medium, largely avoids the problems experienced with monopolar or bipolar electrosurgery. In particular, input power levels are much lower than those generally necessary with a monopolar arrangement (typically 100 watts). Moreover, because of the relatively large spacing between its electrodes, an improved depth of effect is obtained compared with conventional bipolar arrangements.

However, where the volume of a body cavity is small (for example in arthroscopic surgery where even the large joints, such as the knee, may only accommodate 50-60 ml of irrigation fluid) the following problems may occur, namely:
(i) Heated fluid in the immediate vicinity of the tissue contact electrode can cause collateral tissue damage;
(ii) The products of the tissue vaporised by the tissue contact electrode can cause visualisation problems; and
(iii) Soft tissue present in a joint space tends to move about, making it difficult to apply the active electrode to vaporise such tissue.

An arthroscopic electrode may be characterised as short (100 to 200 mm), and rigid with a working diameter up to 5 mm. It can be introduced through a stab incision into a joint cavity (with or without a cannula) using the triangulation technique. Such an electrode is operated with a motion which moves the electrode between the 9 O'Clock and 3 O'Clock positions on the arthroscopic image. As a result, the tissue to be treated is usually approached at a shallow working angle with respect to the axis of the electrode. An arthroscopic electrode thus needs to have an effect consistent with this angled approach to the tissue. The tissue to be treated, such as meniscal cartillage, is commonly dense and of a high electrical impedance. An arthroscope electrode requires output power and voltage settings that reflect the type of tissue being treated, the size of electrode, and the fact that arthroscopists are seeking a speed of effect comparable to that of the mechanical shaver devices they currently employ, albeit with an electrode of smaller dimensions than a shaver blade for improved access.

The specification of our European patent application number 959787 describes a bipolar electrosurgical instrument whose tissue treatment electrode is provided with a plurality of apertures through which vapour bubbles and/or particulate material such as tissue particles can be aspirated from the regions surrounding the tissue treatment electrode. Although this electrosurgical instrument does remove some vapour bubbles and/or particulate material from the region surrounding the tissue treatment electrode, but does not completely remove such material. Consequently, the problem of visualisation can still arise.

BRIEF DESCRIPTION OF THE INVENTION

An aim of the invention is to provide an improved electrosurgical instrument of this type.

The present invention provides an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode having an exposed surface for treating tissue, and the return electrode having a fluid contact surface so as to define, in use, a conductive fluid path that completes an electrical circuit between the tissue treatment electrode and the return electrode, wherein the tissue treatment electrode is provided with at least one aperture through which vapour bubbles and/or particulate material can be aspirated from the region surrounding the tissue treatment electrode, and the tissue treatment electrode and the insulation member are disposed such that there is a gap therebetween forming an additional suction channel.

Preferably, the gap between the tissue treatment electrode and the insulation member extends around a substantial portion of periphery of the tissue treatment electrode, and more preferably, the gap extends around the entire periphery of the tissue treatment electrode.

Advantageously, the tissue treatment electrode has a substantially planar tissue treatment surface. Preferably, however, the tissue treatment surface of the tissue treatment electrode is provided with at least one outwardly-extending projection for concentrating the electric field generated by the tissue treatment electrode in the region surrounding that projection.

Preferably, the insulation member includes a chamber in which the tissue treatment electrode is received. Conveniently, the tissue treatment electrode comprises an upper portion including the exposed tissue treatment surface, and a lower portion depending therefrom. The chamber within the insulation member is preferably provided with at least one shoulder, adapted to cooperate with the lower portion of the tissue treatment electrode in order to retain the tissue treatment electrode within the chamber. In this way, the tissue treatment electrode can be securely mounted within the chamber of the insulation member, while maintaining a peripheral suction channel to assist with the evacuation of fluid, bubbles and tissue debris. Typically, the lower portion comprises a keel portion constituted by a shaped section depending from a central stem.

The instrument may further comprise a pump and a suction tube connecting the or each aperture in the tissue treatment electrode and the suction channel with the pump.

Conveniently, the suction tube is made of an electrically-conductive material, whereby the suction tube constitutes an electrical input from an RF generator to the tissue treatment electrode, and the suction tube is mounted within the instrument shaft.

Conceivably, the keel portion is received within the suction tube in order to connect the tissue treatment electrode to the suction tube. Preferably, the suction tube holds the tissue treatment electrode within the insulation member.

Conceivably, the pump is activated cyclically whereby matter is aspirated in a pulsed fashion. The pump may be activated only when the tissue treatment electrode is powered for tissue vaporisation.

The instrument may further comprise an RF generator having a bipolar output connected to the tissue treatment electrode and the return electrode.

In this case, the pump may be controlled in dependence upon the voltage output characteristics of the RF generator.

Preferably, the exposed end of the tissue treatment electrode extends laterally through a cut-out provided in the insulation member at the distal end portion of the instrument, the fluid contact surface of the return electrode overlying the insulation member in the region of the cut-out.

The tissue treatment electrode may be made of tungsten or of an alloy of tungsten or platinum.

The invention also provides an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode having an exposed surface for treating tissue, and the return electrode having a fluid contact surface so as to define, in use, a conductive fluid path that completes an electrical circuit between the tissue treatment electrode and the return electrode, wherein the exposed tissue treatment surface is essentially planar, the insulation member includes an aperture, and the tissue treatment electrode is mounted with respect to the aperture such that a peripheral gap exists around at least a substantial portion of the circumference of the tissue treatment electrode to form a suction channel through which vapour bubbles and/or particulate material can be aspirated from the region surrounding the tissue treatment electrode.

Preferably, the exposed tissue treatment surface has a first cross-sectional area, the insulation member includes an aperture having a second cross-sectional area, and the second cross-sectional area is slightly greater than that of the first cross-sectional area, with the tissue treatment electrode being received in the aperture such that a peripheral gap exists around at least a substantial portion of the circumference of the tissue treatment electrode.

The invention further provides an electrode unit for an electrosurgical instrument for the treatment of tissue in the presence of an electrically-conductive fluid medium, the electrode unit comprising a shaft having at one end means for connection to an instrument handpiece, and, mounted on the other end of the shaft, an electrode assembly comprising a tissue treatment electrode and a return electrode which is electrically insulated from the tissue treatment electrode by means of an insulation member, the tissue treatment electrode having an exposed end for treating tissue, and the return electrode having a fluid contact surface which is spaced from the tissue treatment electrode in such a manner as to define, in use, a conductive fluid path that completes an electrical circuit between the tissue treatment electrode and the return electrode, wherein the tissue treatment electrode is provided with at least one aperture through which vapour bubbles and/or particulate material can be aspirated from the region surrounding the tissue treatment electrode, and the tissue treatment electrode and the insulation member are disposed such that there is a gap therebetween forming an additional suction channel.

The electrode unit may further comprise a pump for subjecting the distal end portion of the instrument shaft to a sub-atmospheric pressure thereby to aspirate, in use, vapour bubbles and/or particulate material through the or each aperture and the suction channel from the region surrounding the tissue treatment electrode.

Conceivably, the pump is activated cyclically whereby matter is aspirated in a pulsed fashion. The pump may be activated only when the tissue treatment electrode is powered for tissue vaporisation.

The electrode unit may further comprise an RF generator having a bipolar output connected to the tissue treatment electrode and to the return electrode. In this case, the pump may be controlled in dependence upon the voltage output characteristics of the RF generator.

The invention still further comprises an electrosurgical apparatus comprising a radio frequency generator and an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode having an exposed end for treating tissue, and the return electrode having a fluid contact surface which is spaced from the tissue treatment electrode in such a manner as to define, in use, a conductive fluid path that completes an electrical circuit between the tissue treatment electrode and the return electrode, and the radio frequency generator having a bipolar output connected to the electrodes, wherein the tissue treatment electrode is provided with at least one aperture, through which vapour bubbles and/or particulate material can be aspirated from the region surrounding the tissue treatment electrode, and the tissue treatment electrode and the insulation member are disposed and that there is a gap therebetween forming an additional suction channel.

The invention further provides an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode having an exposed surface for treating tissue, and the return electrode having a fluid contact surface so as to define, in use, a conductive fluid path that completes an electrical circuit between the tissue treatment electrode and the return electrode, wherein the insulation member includes a chamber in which the tissue treatment electrode is received, the tissue treatment electrode comprises an upper portion including the exposed tissue treatment surface, and a lower portion depending therefrom, and the chamber is provided with at least one shoulder, adapted to cooperate with the tissue treatment electrode in order to retain the tissue treatment electrode within the chamber.

As previously described, at least one aperture is preferably provided through which vapour bubbles and/or particulate material can be aspirated from the region surrounding the tissue treatment electrode, and the instrument further comprises a suction tube connecting the or each aperture to a source of suction. In one arrangement the lower portion of the tissue treatment electrode comprises a keel portion, and the keel portion is received within the suction tube in order to connect the tissue treatment electrode to the suction tube and hold the tissue treatment electrode within the chamber.

By mounting the tissue treatment electrode in this way, the electrode is located within the body of the chamber, and need not have a physical connection with the periphery of the chamber. Thus, the tissue treatment electrode is conveniently mounted within the chamber so that there is a gap between the tissue treatment electrode and the insulation member thereby forming a suction channel. The gap between the tissue treatment electrode and the insulation member conveniently extends around a substantial portion of periphery of the tissue treatment electrode, and may even extend around the entire periphery of the tissue treatment electrode.

BRIEF DESCRIPTION OF THE DRAWINGS

The invention will now be described in greater detail, by way of example, with reference to the drawings, in which.

DETAILED DESCRIPTION OF THE INVENTION

Figure 1:
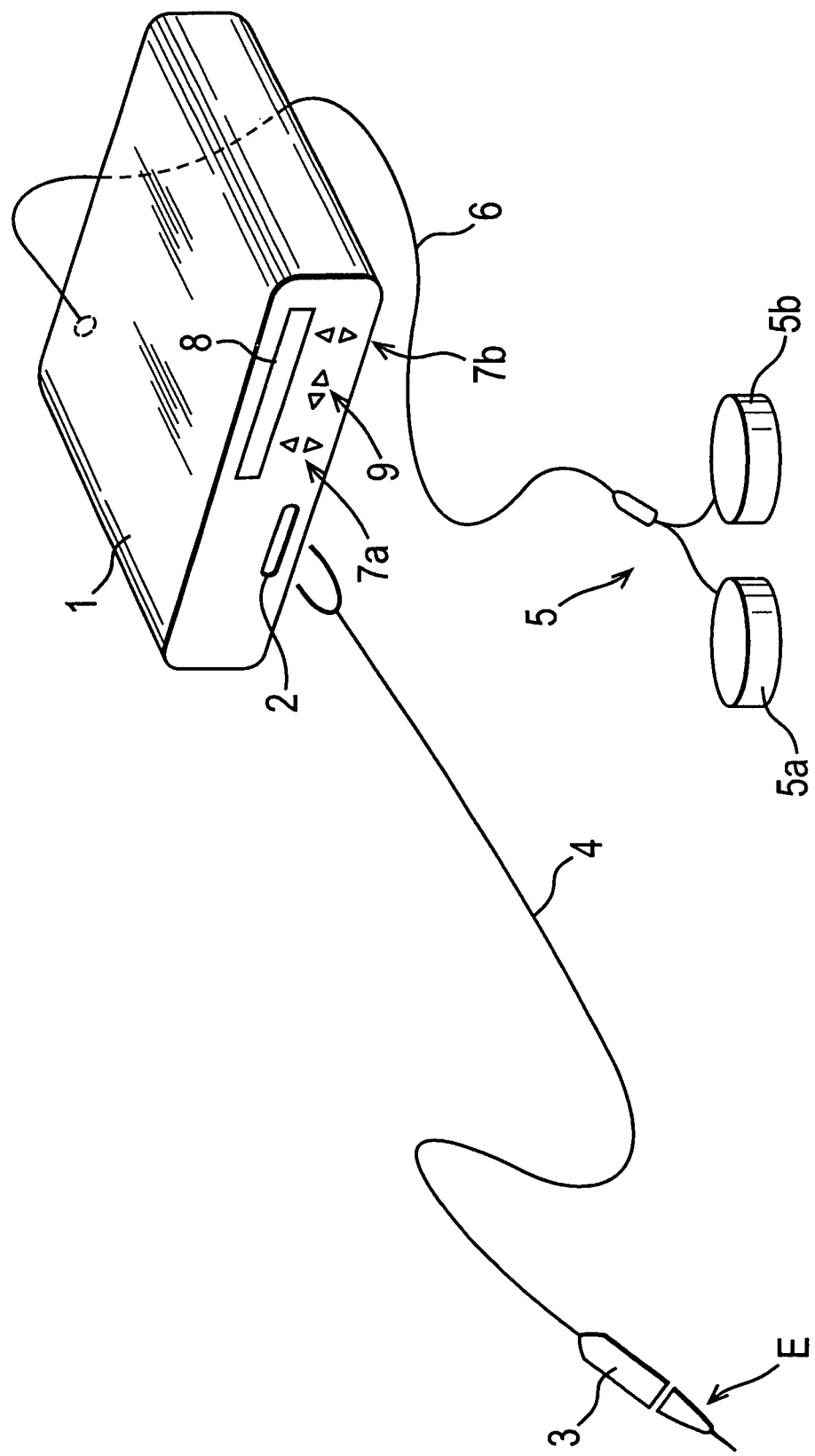
FIG. 1 is a diagram showing an electrosurgical apparatus constructed in accordance with the invention.
Figure 2:
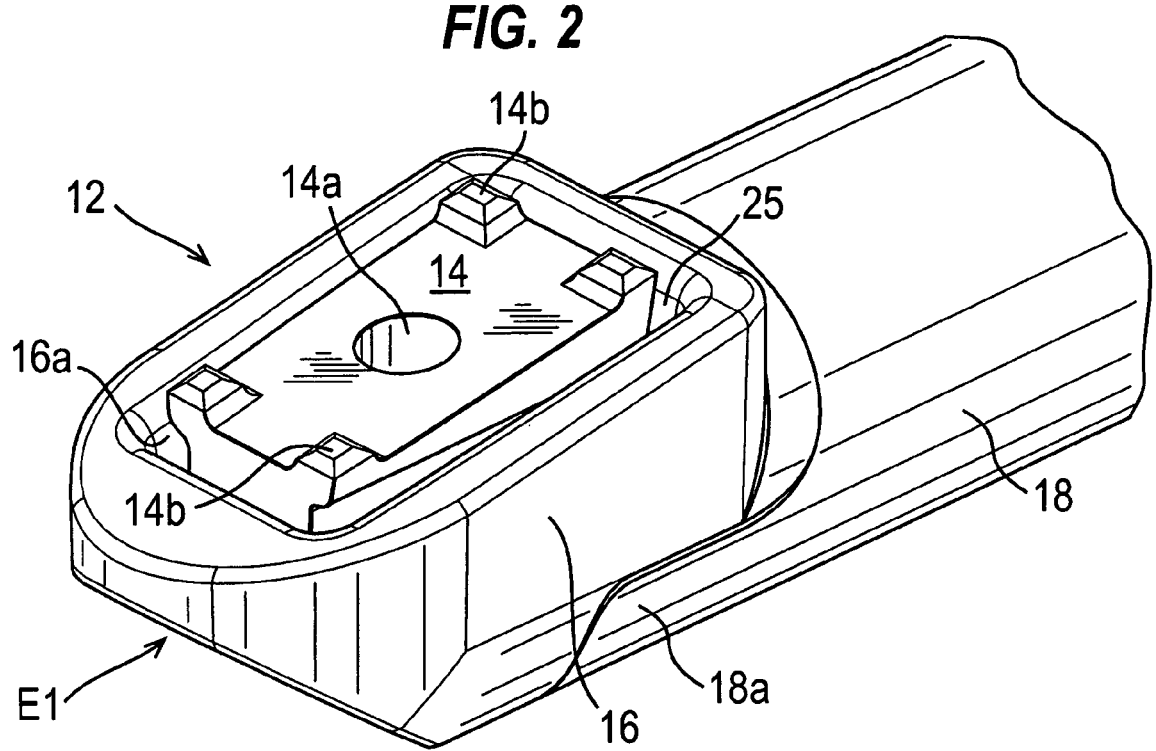
FIG. 2 is a perspective view of the distal end of a first form of electrosurgical instrument constructed in accordance with the invention.
Figure 3:
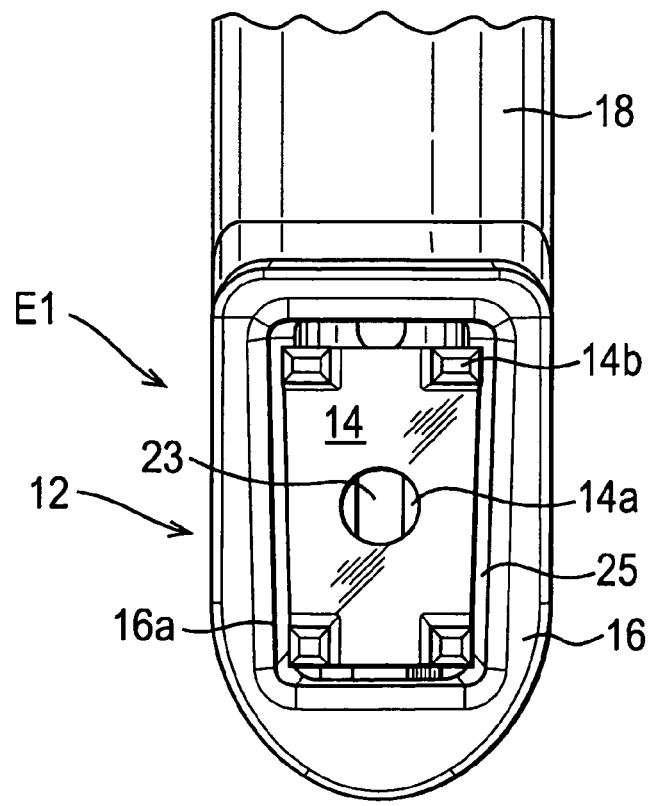
FIG. 3 is a plan view corresponding to FIG. 2.

Referring to the drawings, FIG. 1 shows electrosurgical apparatus including a generator 1 having an output socket 2 providing a radio frequency (RF) output, via a connection cord 4, for an instrument in the form of a handpiece 3. Activation of the generator 1 may be performed from the handpiece 3 via a control connection (not shown) in the cord 4, or by means of a footswitch unit 5 connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9 are provided as an alternative means for selection between the desiccation and vaporisation modes.

The handpiece 3 has an active tip E at its distal end, such as the active tips E1 and E2 to be described below.

FIGS. 2 to 6 show a first embodiment of active tip E1 with an electrode assembly 12 comprising an active electrode 14 received in a ceramic insulator 16. The active electrode 14 is housed within an aperture 16a provided in the ceramic insulator 16. The active (tissue treatment) electrode 14 is formed of tungsten or an alloy of tungsten and platinum. The active electrode 14 is formed with a suction aperture 14a, and is provided with a respective projection 14b at each of its corners, the projections being provided to concentrate the electric field in each of the corners of the active electrode. The projections 14b also serve to create a small separation between the planar surface of the active electrode 14 and the tissue to be treated. This allows conductive fluid to circulate over the planar surface, and avoids overheating of the electrode or the tissue.

Figure 4:
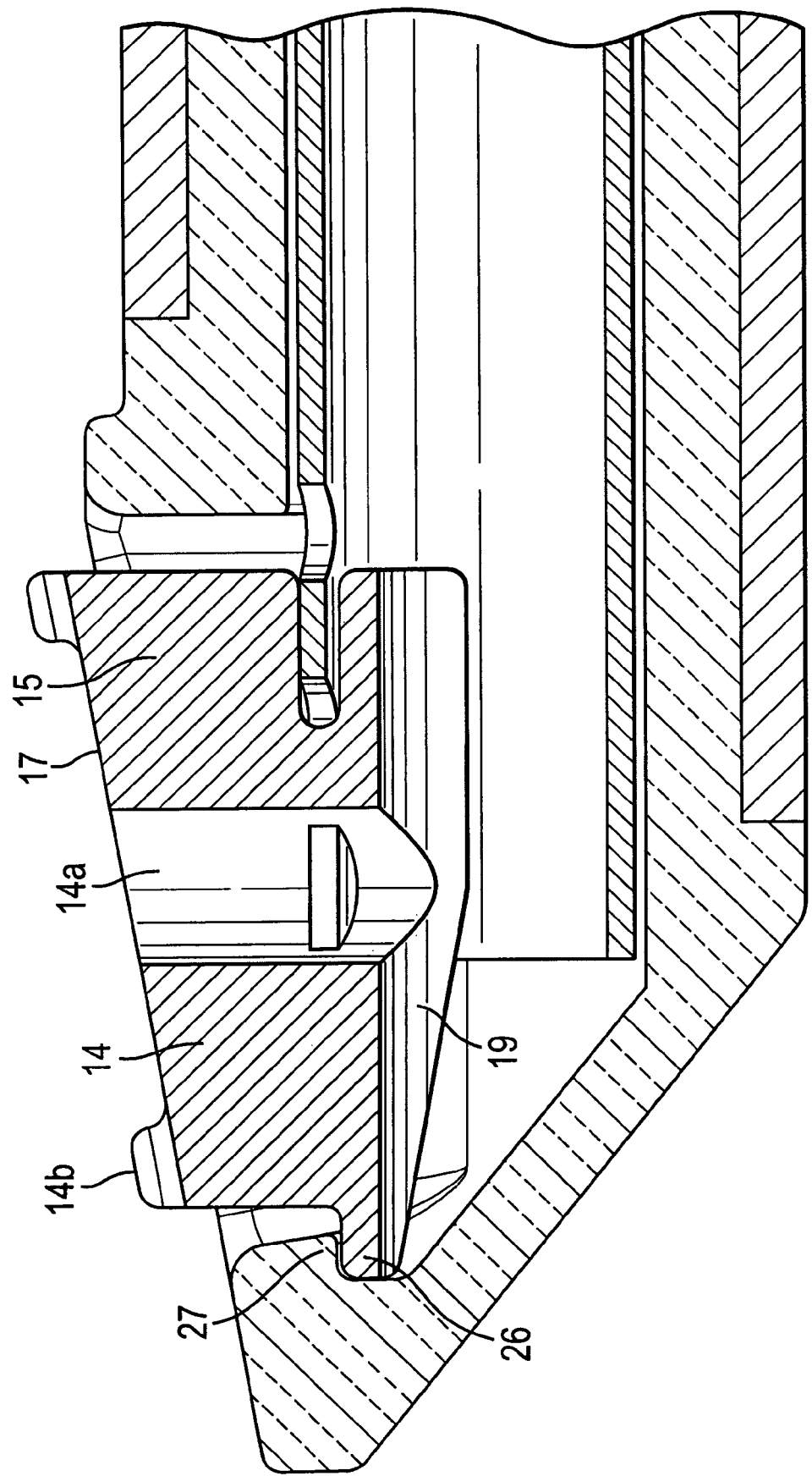
FIG. 4 is a diagramatic, cross-sectional side elevation corresponding to FIGS. 2 and 3.
Figure 5:
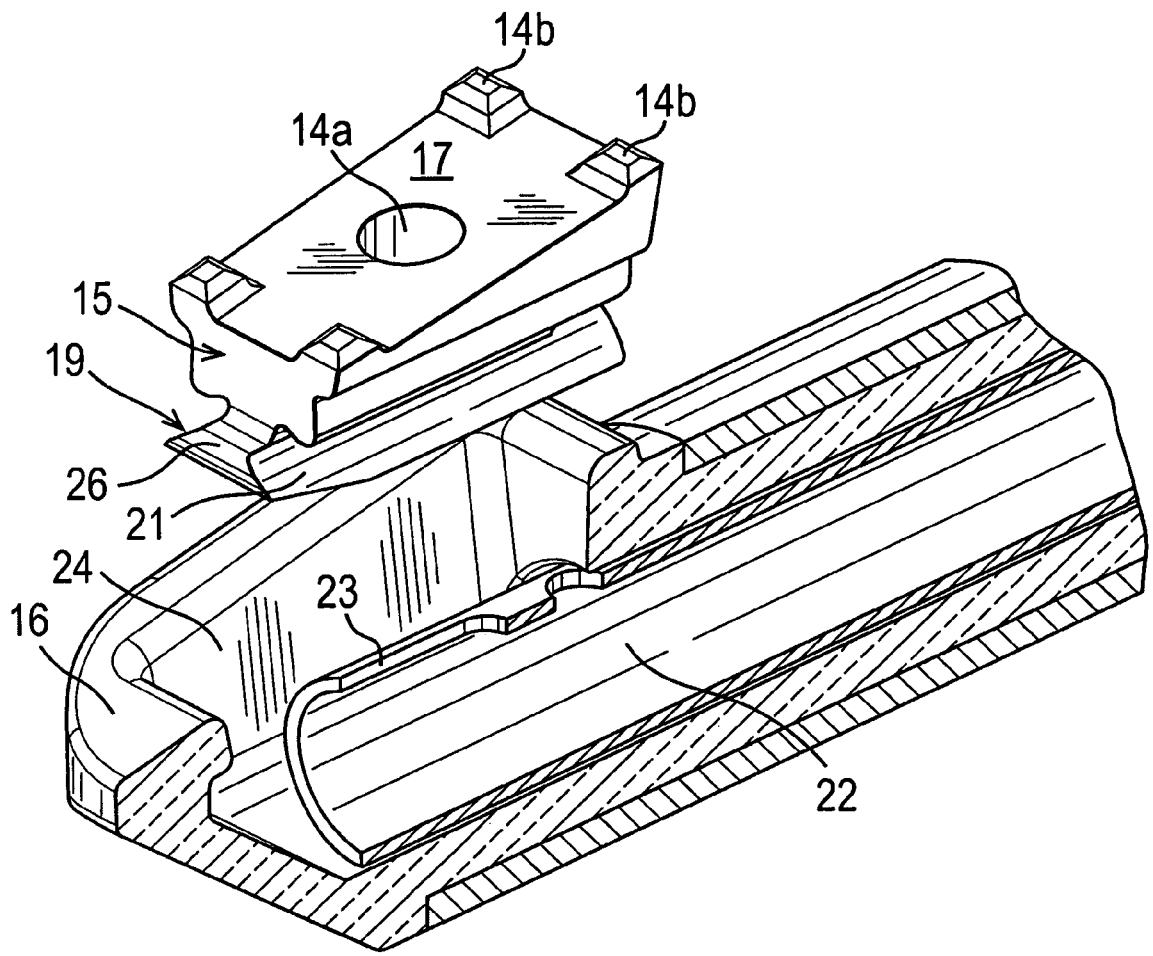
FIG. 5 is an exploded view, partly in section, corresponding to FIGS. 2 to 4.
Figure 6:
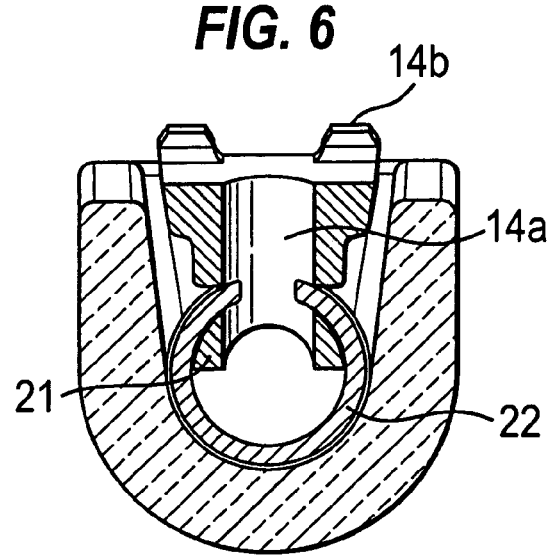
FIG. 6 is a cross-sectional view corresponding to FIGS. 2 to 4.

As shown in FIGS. 4 to 6, the active electrode 14 comprises an upper portion 15 including the planar surface 17 and the projections 14b, and a lower portion 19 including a shaped keel portion 21. To assembly the active tip E1, the active electrode is lowered into a chamber 24 present within the ceramic insulator 16. A suction tube 22, is then pushed forward to locate over the keel portion 21 of the active electrode and secure it in place. The forward movement of the suction tube 22 pushes the active electrode 14 forwardly in the chamber 24, such that a projection 26 on the distal end of the keel locates under a corresponding shoulder 27 present on the ceramic insulator 16, thereby locking the active electrode in place. This is shown in detail in FIGS. 4 & 5.

In order to reduce the problems of vapour bubble production and to assist with the removal of particulate material (such as tissue debris) from the region surrounding the tissue treatment electrode 14, the active tip E1 is provided with a suction pump (not shown) which can remove vapour bubbles via the shaft of the instrument through the aperture 14a in the active electrode. The suction tube 22 is made of an electrically-conductive material such as stainless steel or gold-plated copper, and connects the suction aperture 14a to the suction pump. The tube 22 also constitutes means for electrically connecting the active electrode 14 to the generator 1.

The RF generator 1 (not shown in FIG. 2) delivers an electrosurgical current to the electrode assembly 12. The generator 1 includes means for varying the delivered output power to suit different electrosurgical requirements. The generator may be as described in the specification of our European Patent No. 754437.

A return electrode 18 is constituted by the distal end portion of the shaft 10, and a polytetrafluorethylene, a polyolefin, a polyester or ethylene tetrafluoroethylene sleeve 20 surrounds the proximal portion of the shaft 10 adjacent to the return electrode 18. The return electrode 18 is formed with a hood-like extension 18a which extends over the surface of the insulator 16 which is opposite to the aperture 16a. The active tip E1 can, thus, provide maximum tissue engagement for shallow working angle applications, and is known as a side-effect electrode.

The suction tube 22 is formed with a longitudinal slot 23 at its distal end. As shown in the figures, the distal end of the suction tube 22 extends into the chamber 24 defined by the ceramic insulator 16 beneath the active electrode 14. The slot 23 is contiguous with the aperture 14a in the active electrode 14, and with a peripheral channel 25 defined between the external periphery of the active electrode and the internal periphery of the aperture 16a.

This enhances the elimination of vapour bubbles and particulate material from an operation site, which is particularly advantageous during aggressive tissue debulking. The suction pump may be controlled so that the flow of bubbles and particulate material through, and from around, the electrode 14 is balanced to the voltage output characteristics of the RF generator 1 to prevent excessive cooling of the active electrode and a resultant increase in its vaporisation power threshold. The thermal mass of the fenestrated active electrode 14 is lower than that of a solid form active electrode, and this assists in rapidly re-establishing the vapour pocket around the active electrode should this collapse following excessive cooling.

FIGS. 7 to 10 show the second form of active tip E2 at the distal end of the electrosurgical instrument handpiece 3. The active tip E2 is similar to the tip E1, so like reference numerals will be used for like parts, and only the differences will be described in detail.

Figure 7:
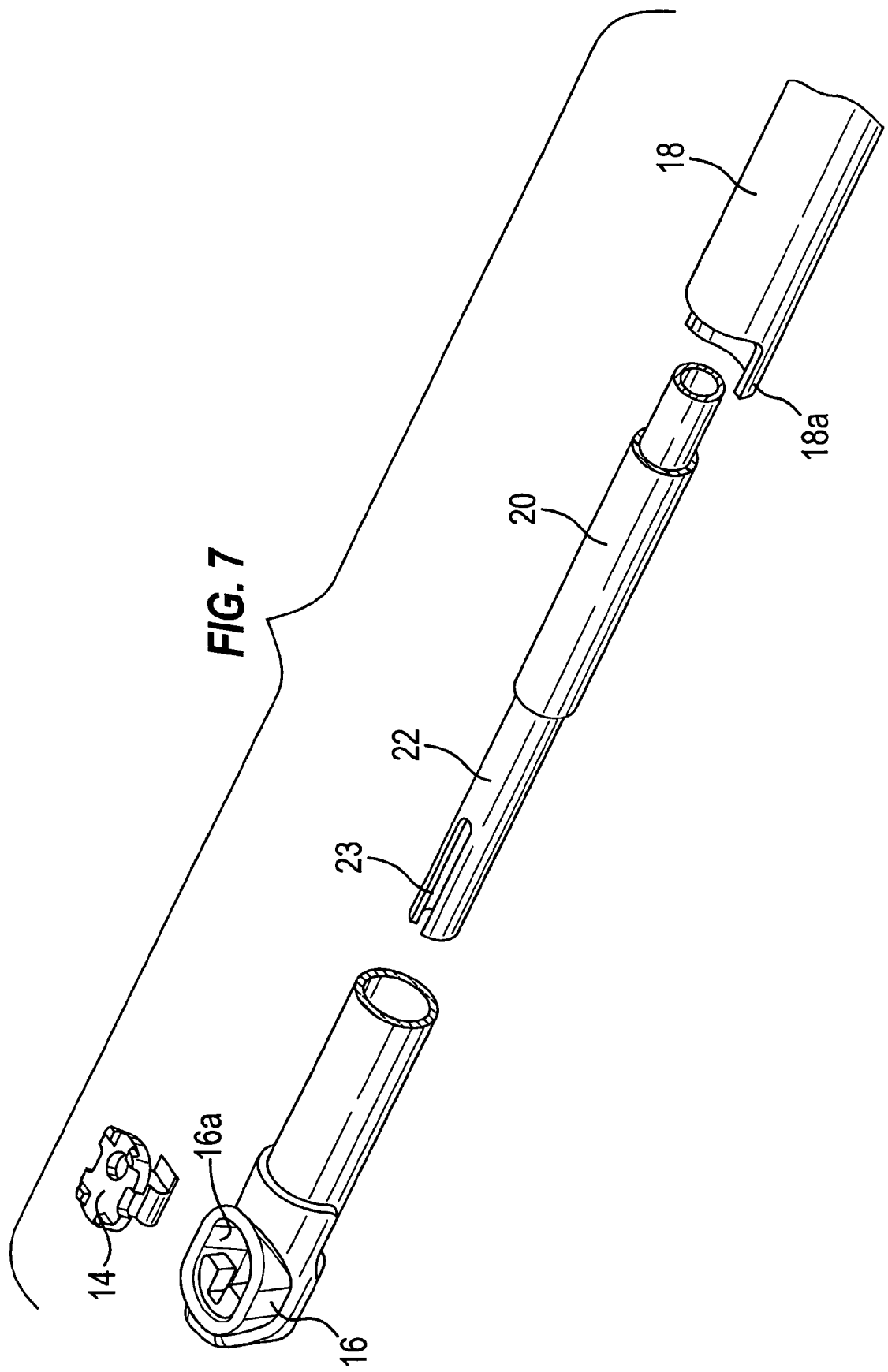
FIG. 7 is a perspective view, partly in section, of the distal end of a second form of electrosurgical instrument constructed in accordance with the invention.
Figure 8:
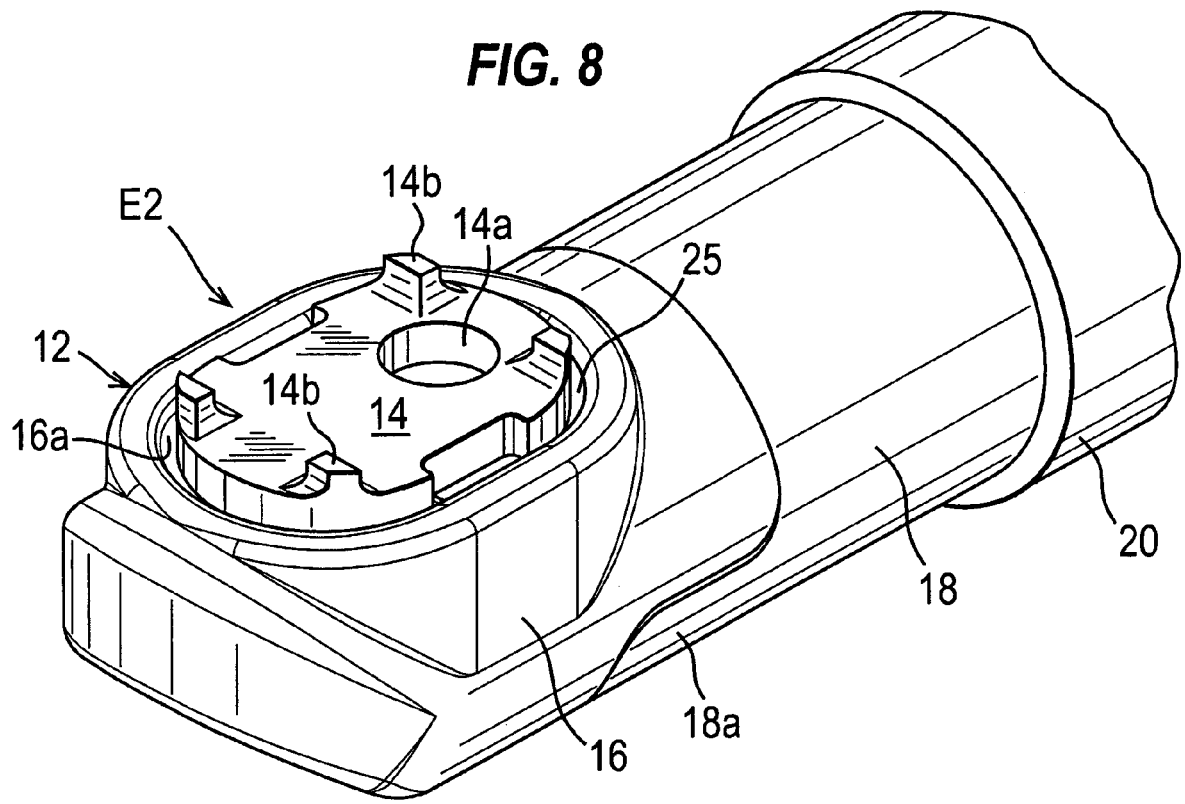
FIG. 8 is a perspective view of the distal end of the electrosurgical instrument of FIG. 7.
Figure 9:
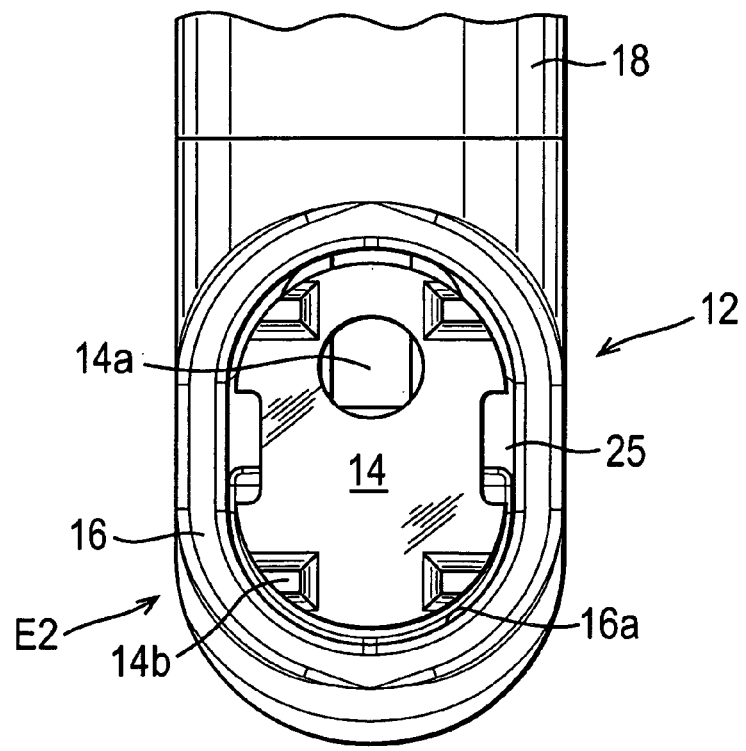
FIG. 9 is a plan view corresponding to FIG. 8.

One difference between the electrode unit E2 and the electrode unit E1 is the position of the suction aperture 14a, the suction aperture of the electrode unit E2 not being positioned centrally but towards the proximal end portion of the active electrode 14. However, the main difference is in the way in which the active electrode 14 is assembled within the ceramic insulator 16. In the embodiment of FIGS. 7 to 9, the chamber 24 within the ceramic insulator 16 is not empty, but contains a shelf portion 28 on each side of the chamber, with a slot 29 therebetween. To assemble the active electrode within the ceramic insulator, the active electrode 14 is lowered into the chamber 24, with the keel portion 21 being received in the chamber proximally of the shelf portions 28. The keel portion 21 comprises a shaped lower section 30, depending from a narrower stem 31. When the active electrode has been introduced into the chamber 24, it can then be moved forwardly such that the stem 31 is received in the slot 29 between the shelf portions 28, with the lower section 30 being retained under the shelf portions 28. With the active electrode in this position, the suction tube 22 is then moved distally to fit around the lower section 30 to lock the active electrode 14 in position. This locking mechanism holds the active electrode firmly within the ceramic insulator 16, and ensures that the active electrode 14 is not displaced, even if significant forces are applied to the instrument during use.

Figure 11:
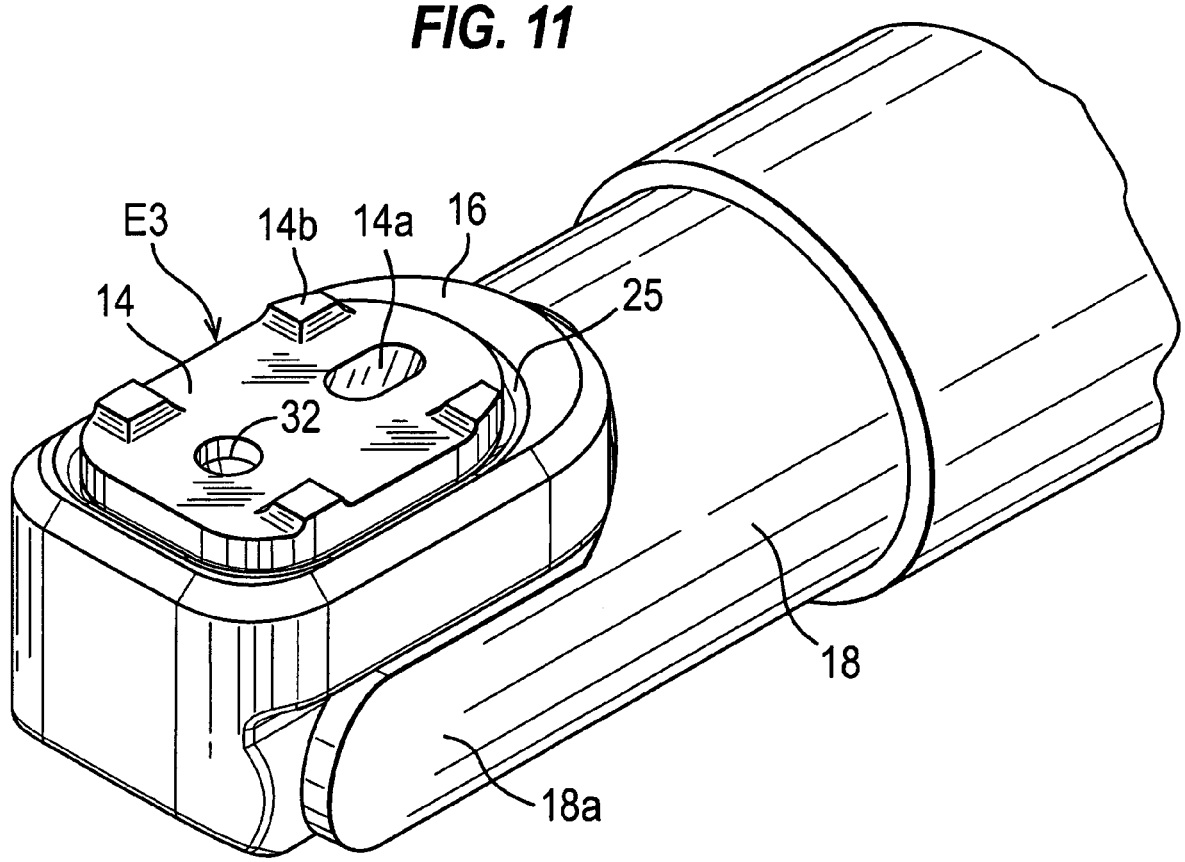
FIG. 11 is a perspective view of the distal end of a third form of electrosurgical instrument constructed in accordance with the invention.
Figure 12:
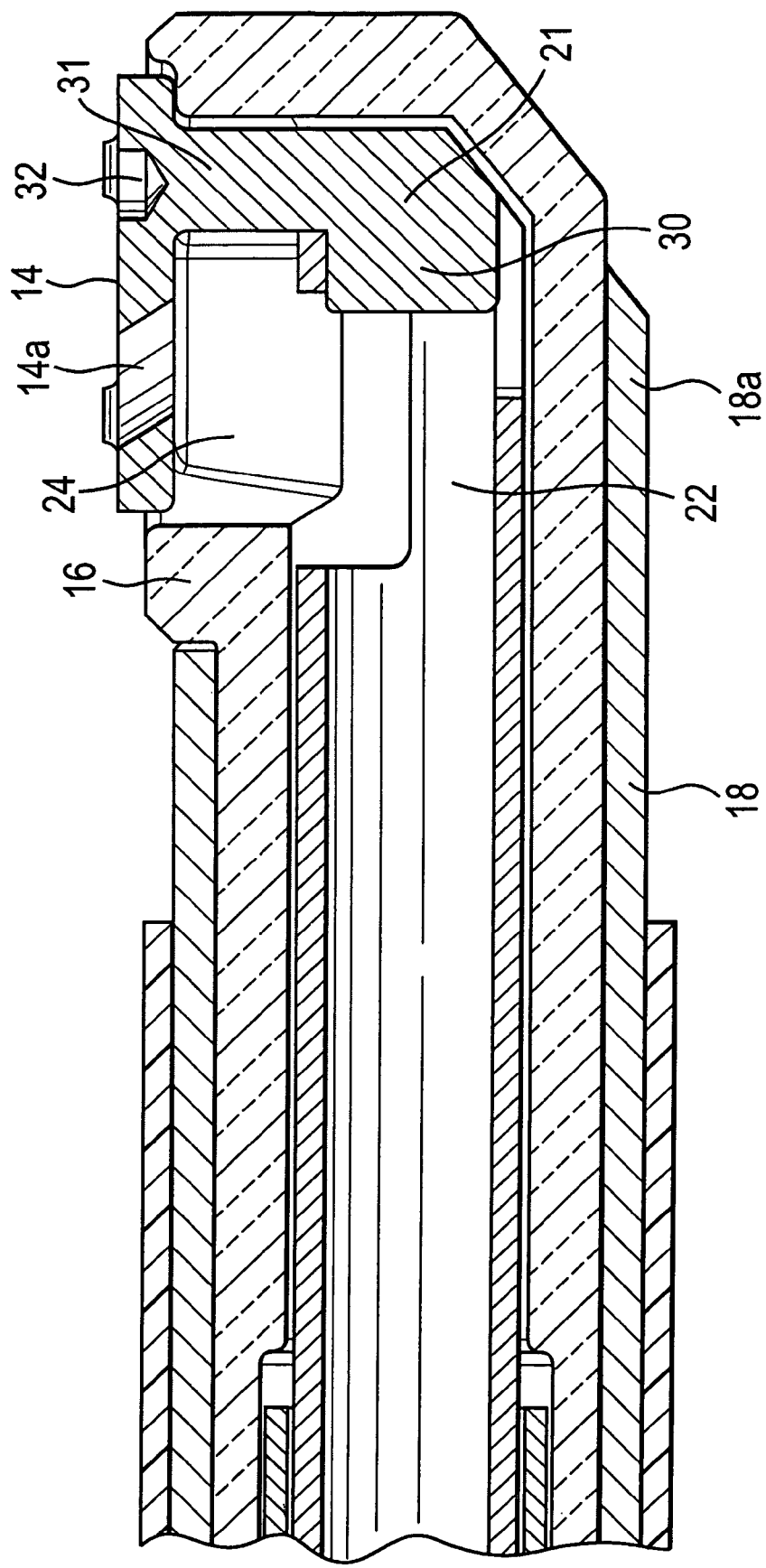
FIG. 12 is a sectional side view of the electrosurgical instrument of FIG. 11.
Figure 13:
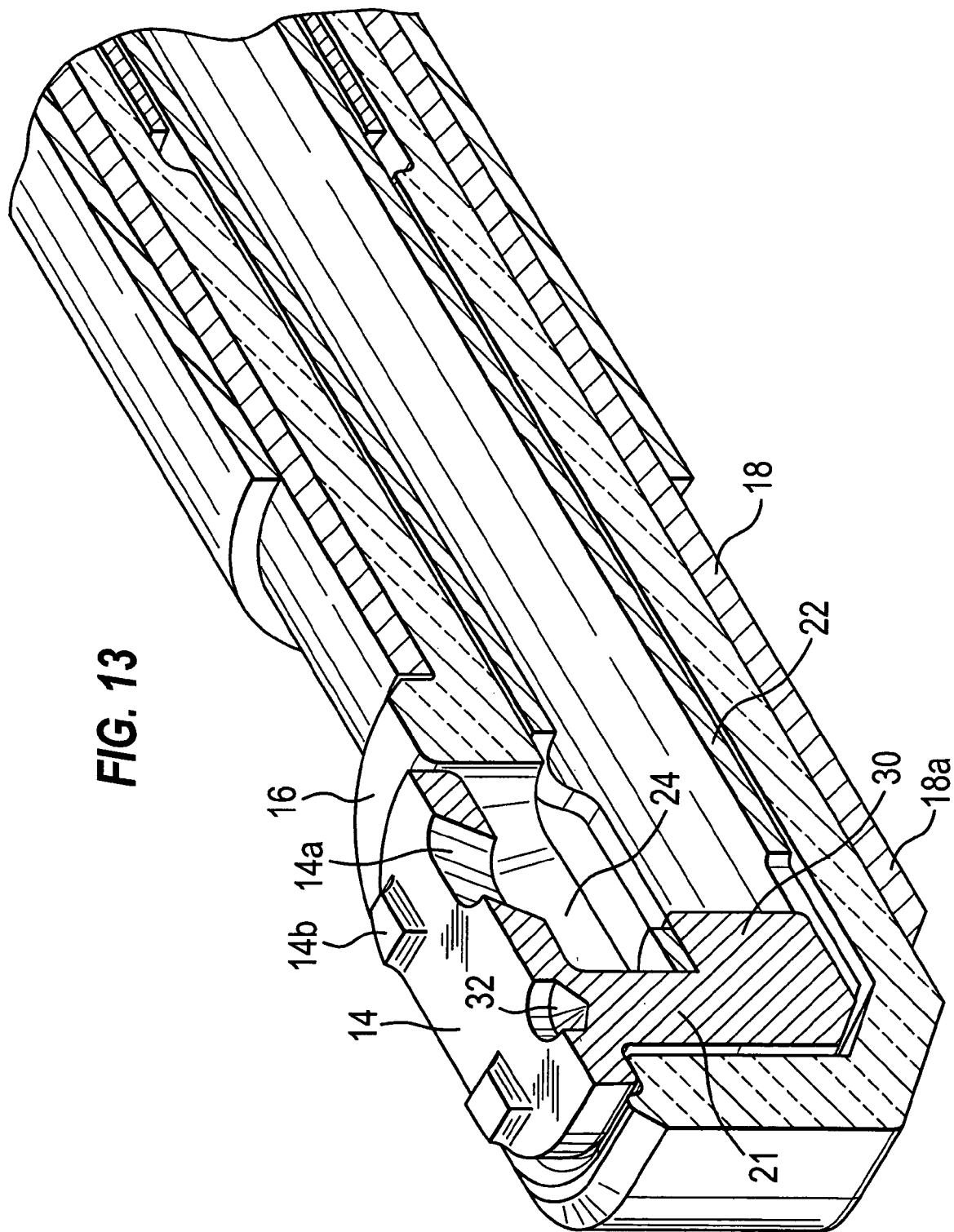
FIG. 13 is a sectional perspective view of the electrosurgical instrument of FIG. 11.

FIGS. 11 to 13 show the third form of active tip E3 at the distal end of the electrosurgical instrument handpiece 3. The active tip E3 is similar to the tip E2, so like reference numerals will be used for like parts, and only the differences will be described in detail.

Figure 10:
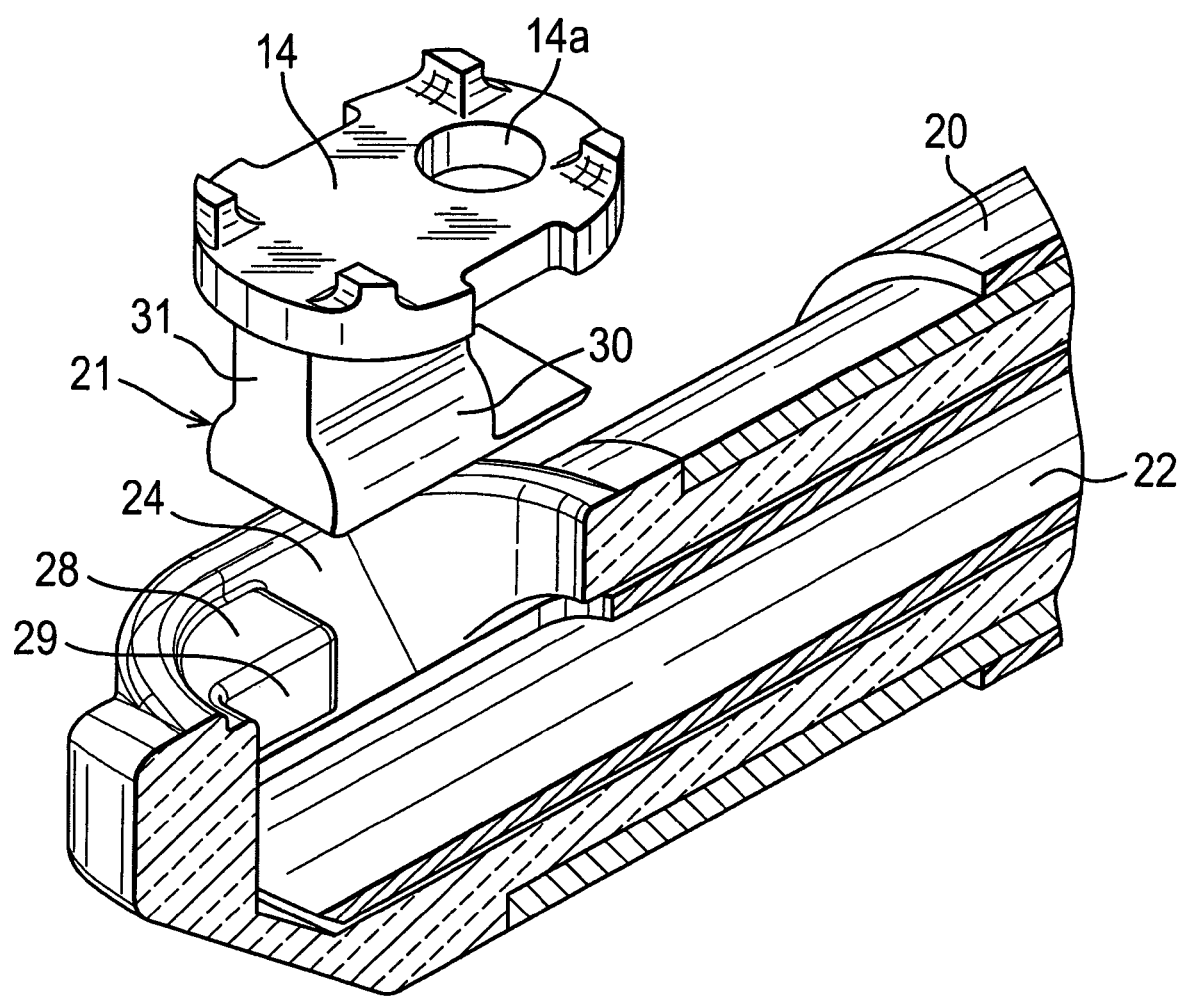
FIG. 10 is an exploded view, partly in section corresponding to FIGS. 8 and 9.

The active tip E3 is secured in the insulator 16 in similar fashion to the embodiment of FIGS. 7 to 10, with the keel portion 21 being received within the suction tube 22, which is used to lock the active tip in the chamber 24 under the shelf portions 28 (see FIG. 10). The active tip E3 is slightly different in that the aperture 14a slopes through the tissue treatment electrode at an angle of approximately 45 degrees. A blind recess 32 is provided in the electrode 14. This recess 32 is provided purely to allow for the automated assembly of the electrosurgical instrument, and does not provide a suction aperture as it does not pass all the way through the electrode 14.

Whichever assembly arrangement is employed, the upper portion 15 of the active electrode 14 is located within the ceramic insulator 16 such that a peripheral suction channel 25 exists between the active electrode and the insulator. This peripheral channel, in addition to the suction aperture 14a, helps to draw fluid, bubbles and tissue debris away from the active electrode and into the suction tube 22.

These electrosurgical instruments are particularly useful for rapid tissue debulking. One of the problems which could be encountered when tissue is rapidly debulked using an arthroscopic electrode configuration, particularly when working in small joint spaces, is the production of vapour bubbles generated as an end product of tissue vaporisation. Such bubbles obscure vision, and can coalesce at the site of tissue application, so that the electrical circuit between the active and return electrodes becomes compromised by the absence of conductive fluid.

The use of the electrosurgical instrument of FIGS. 2 to 6, FIGS. 7 to 10, or FIGS. 11 to 13 however, leads to a further reduction in the production of vapour bubbles as a result of the lower threshold power of vaporisation which results from use of the active tip E1, E2 or E3. This improvement results from the hood-like extension 18a of the return electrode 18, which extends over the back of the active electrode 14. This reduces the separation between the active electrode 14 and the return electrode 18, thereby reducing the electrical field and the vaporisation threshold power of the active electrode. This enhances the speed of vaporisation of the tissue at a lower power than would otherwise be required for the given active electrode area, and hence reduces the formation of vapour bubbles. As the hood-like extension 18a extends along a major portion of length of the active electrode 14, a large active electrode size can be supported, despite the reduction in electrode separation.

The robustness of the electrode assembly 12 of each of the active tips E1 to E3 is also important in arthroscopic surgery, both because of the tendency of surgeons to use an electrode assembly as a cold manipulator, and because of the rigid nature of the tissue to be treated—particularly bone and cartilage. The hood-like extension 18a adds mechanical strength to the electrode assembly 12, as it extends over the ceramic insulator 16, thereby reducing the risk of ceramic fracture and potential breakdown of insulation.

These electrosurgical instruments are intended primarily for use in arthroscopic surgery which requires rapid tissue debulking by vaporisation. In use, such electrosurgical instrument is manipulated to introduce its electrode assembly 12 into a selected operation site (for example, within the joint space of a knee), so that its active electrode 14 contacts the tissue to be treated, and with the tissue and the electrode assembly immersed in saline.

The footswitch 5b (or the push button 7b) is then operated to set the required power level for vaporisation. The generator 1 then provides sufficient RF power to the associated electrode assembly 12 to vaporise the saline surrounding its active electrode 14, and to maintain a vapour pocket surrounding this electrode. Using a brushing technique, with firm pressure against the tissue surface, rapid debulking of the tissue is achieved. Gently touching the tissue will reduce the effect, and can be used to sculpture and smooth the residual tissue surface. With tissue engagement, provided the geometry of the active electrode 14 is appropriate for the application, the flow of irrigant through the active electrode will be reduced, the amount of reduction depending on the nature of the tissue surface, the application pressure and the suction pressure. Speed of debulking will, therefore, depend on these variables. Once the vaporisation occurs, the products will include vapour bubbles, carbon particles and tissue debris. All of these products are removed from the region of the active electrode 14 by aspiration caused by the suction pump. The aperture 14a and the peripheral channel 25 are positioned so that vaporised tissue is drawn into the instrument, and then evacuated through the instrument shaft 10, by the aspiration of the suction pump.

The active tips E1 to E3 are also very effective in removing heated saline (distension fluid) from within a joint cavity. The risk of hot distension fluid occurs primarily during power application to reach the vaporisation threshold. Once the threshold has been reached, the power requirement falls by 30-50%.

Whilst aspiration through the active electrode 14 will remove heated saline from the body cavity, and remove any risk of overheating through prolonged activation under conditions where the vaporisation threshold is not reached, the cooling effect and disruption of vapour pockets created around the active electrode will increase the vaporisation threshold. A vicious cycle can, therefore, be created, wherein the more suction applied through the active electrode 14, the more power required to reach the vaporisation threshold, and the greater the risk of heating. The other factor influencing the vaporisation threshold is the ratio of return active contact area, and the insulation separation between the two electrodes 14 and 18. The size of the active electrode 14 and the insulation separation must, therefore, be reduced to the minimum necessary to achieve the function in order to offset the effects of aspiration in elevating the power threshold of vaporisation.

The specification of our European Patent No. 959784 discloses techniques for controlling the vaporisation threshold by employing active electrode designs which assist in capturing vapour pockets and preventing cooling of the active electrode application site by screening from the flow of irrigant provided by channels in an endoscope.

Although the electrosurgical instrument is intended primarily for use in the vaporisation of tissue, it can also be used for desiccation, particularly of synovial membranes or to separate muscle attachments. In this case, once its electrode assembly 12 has been introduced into a selected operation site, the RF generator 1 is actuated using the footswitch 5a or the push button 7a to set the required power level for desiccation. The generator 1 will then provide sufficient RF power to the electrode assembly 12 to maintain the saline adjacent to the active electrode 14 substantially at its boiling point without creating a vapour pocket surrounding that electrode. The instrument can then be manipulated by moving the electrode 14 across the surface of the tissue to be treated in a side-to-side "painting" technique.

The electrosurgical instrument can also be used for delivering a blended power output. This is achieved by automatically alternating the output of the RF generator 1 between the desiccation and vaporisation power levels, so that more haemostasis is produced then is possible in the vaporisation mode. As a consequence. the speed of tissue debulking is reduced, but the increased haemostasis is useful when cutting or debulking vascular tissue structures. Alternatively, the output of the RF generator 1 can be pulsed at the vaporisation power level, without cycled activation of the desiccation mode. This produces a less aggressive tissue vaporisation than occurs in the vaporisation mode, with a consequent reduction in both bubble formation and the risk of tissue charring.

Each of the active tips E1 to E3 has the additional advantage that the aspiration in the region of the active electrode 14 restricts the flow of convection currents in the saline surrounding the electrode assembly 12. As the power threshold required to reach vaporisation is dependent on the power dissipation of the active electrode 14 and the flow characteristics around it, the power threshold is dependent upon the maximum rate of convection. Consequently, the restriction of the convection currents reduces the power threshold, and this is advantageous as it enables the use of a cheaper RF generator, as well as avoiding problems such as dissipation within the instrument, and catastrophic overheating of the active electrode. It also facilitates control of the generators once vaporisation commences. The importance of power threshold of vaporisation is discussed in greater detail in the specification of our European Patent No. 959784.

Another advantage of these electrode units is that in use, the active electrode 14 faces down, so that saline heated thereby rises to the return electrode 18. This leads to a reduction of impedance throughout the circuit, and hence to a reduction of the heat dissipation in the saline path. Throughout this specification, the term "pump" should be construed to include any suitable controlled vacuum source.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. An electrosurgical instrument for the treatment of tissue in the presence of an electrically-conductive fluid medium, the instrument comprising:
    an instrument shaft, and
    an electrode assembly at one end of the shaft, the electrode assembly comprising:
        a tissue treatment electrode,
        a return electrode, and
        an insulation member that electrically insulates the tissue treatment electrode from the return electrode,
    an exposed surface of the tissue treatment electrode forming a tissue treating surface, the majority of the tissue treating surface being substantially planar, and
    the return electrode having a fluid contact surface so as to define, in use, a conductive fluid path that completes an electrical circuit between the tissue treatment electrode and the return electrode,
    the insulation member including an aperture, and the tissue treatment electrode being mounted within the aperture, such that a peripheral channel is defined between an outer perimeter of the tissue treatment electrode and an inner perimeter of the insulation member aperture and extends around at least a substantial portion of the outer perimeter of the tissue treatment electrode to form a suction channel through which vapour bubbles and/or particulate material can be aspirated from the region surrounding the tissue treatment electrode.

2. The electrosurgical instrument as claimed in claim 1, wherein the channel extends around the entire periphery of the tissue treatment electrode.

3. The electrosurgical instrument as claimed in claim 1, wherein the tissue treatment surface of the tissue treatment electrode is provided with at least one outwardly-extending projection for concentrating the electric field generated by the tissue treatment electrode in the region surrounding that projection.

4. The electrosurgical instrument as claimed in claim 1, wherein the insulation member includes a chamber in which the tissue treatment electrode is received.

5. The electrosurgical instrument as claimed in claim 4, wherein the tissue treatment electrode comprises an upper portion including the exposed tissue treatment surface, and a lower portion depending therefrom.

6. The electrosurgical instrument as claimed in claim 5, wherein the chamber within the insulation member is provided with at least one shoulder adapted to cooperate with the lower portion of the tissue treatment electrode in order to retain the tissue treatment electrode within the chamber.

7. The electrosurgical instrument as claimed in claim 1, further comprising a pump and a suction tube connecting the or each aperture in the tissue treatment electrode and the suction channel with the pump.

8. The electrosurgical instrument as claimed in claim 7, wherein the suction tube is made of an electrically-conductive material, whereby the suction tube constitutes an electrical input from an RF generator to the tissue treatment electrode.

9. The electrosurgical instrument as claimed in claim 8, wherein the suction tube is mounted within the instrument shaft.

10. The electrosurgical instrument as claimed in claim 9, wherein the lower portion of the tissue treatment electrode comprises a keel portion.

11. The electrosurgical instrument as claimed in claim 10, wherein the keel portion is received within the suction tube in order to connect the tissue treatment electrode to the suction tube.

12. The electrosurgical instrument as claimed in claim 11, wherein the suction tube holds the tissue treatment electrode within the insulation member.

13. The electrosurgical instrument as claimed in claim 1, further comprising an RF generator having a bipolar output connected to the tissue treatment electrode and the return electrode.

14. The electrosurgical instrument as claimed in claim 1, wherein the exposed end of the tissue treatment electrode extends laterally through a cut-out provided in the insulation member at the distal end portion of the instrument, the fluid contact surface of the return electrode overlying the insulation member in the region of the cut-out.

15. The electrosurgical instrument as claimed in claim 1, wherein the cross-sectional area of the aperture is slightly greater than the cross-sectional area of the tissue treatment surface, the tissue treatment electrode being received in the aperture such that a peripheral channel exists around at least a substantial portion of the circumference of the tissue treatment electrode.

16. The electrosurgical instrument as claimed in claim 1, wherein the tissue treatment electrode is provided with at least one aperture through which vapour bubbles and/or particulate material can be additionally aspirated from the region surrounding the tissue treatment electrode.

17. The electrosurgical instrument as claimed in claim 1, wherein the peripheral channel extends continuously around more than half of the outer perimeter of the tissue treatment electrode.

18. An electrosurgical instrument for the treatment of tissue in the presence of an electrically-conductive fluid medium, the instrument comprising:
an instrument shaft, and
an electrode assembly at one end of the shaft, the electrode assembly comprising:
a tissue treatment electrode,
a return electrode, and
an insulation member that electrically insulates the tissue treatment electrode from the return electrode,
the tissue treatment electrode having an exposed surface for treating tissue, and
the return electrode having a fluid contact surface so as to define, in use, a conductive fluid path that completes an electrical circuit between the tissue treatment electrode and the return electrode,
the insulation member including a chamber in which the tissue treatment electrode is mounted,
the tissue treatment electrode comprising an upper portion including the exposed tissue treatment surface, and a lower portion depending therefrom, and
the insulation member chamber including at least one shoulder that engages the lower portion of the tissue treatment electrode in order to retain the tissue treatment electrode within the insulation member chamber.

19. The electrosurgical instrument as claimed in claim 18, wherein at least one aperture is provided through which vapour bubbles and/or particulate material can be aspirated from the region surrounding the tissue treatment electrode, and the instrument further comprises a suction tube connecting the or each aperture to a source of suction.

20. The electrosurgical instrument as claimed in claim 19, wherein the lower portion of the tissue treatment electrode comprises a keel portion.

21. The electrosurgical instrument as claimed in claim 20, wherein the keel portion is received within the suction tube in order to connect the tissue treatment electrode to the suction tube and hold the tissue treatment electrode within the chamber.

22. The electrosurgical instrument as in claim 18, wherein the tissue treatment electrode is mounted within the chamber such that there is a channel between the tissue treatment electrode and the insulation member thereby forming a suction channel.

23. The electrosurgical instrument as claimed in claim 22, wherein the channel between the tissue treatment electrode and the insulation member extends around a substantial portion of periphery of the tissue treatment electrode.

24. The electrosurgical instrument as claimed in claim 23, wherein the channel extends around the entire periphery of the tissue treatment electrode.

* * * * *